United States Patent
Yoshida et al.

(10) Patent No.: US 9,597,710 B2
(45) Date of Patent: Mar. 21, 2017

(54) METHOD FOR MANUFACTURING ULTRASOUND TRANSDUCER

(71) Applicant: OLYMPUS CORPORATION, Tokyo (JP)

(72) Inventors: Satoshi Yoshida, Koshigaya (JP); Takuya Imahashi, Kawasaki (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/059,499

(22) Filed: Mar. 3, 2016

(65) Prior Publication Data

US 2016/0184863 A1 Jun. 30, 2016

Related U.S. Application Data

(63) Continuation of application No. PCT/JP2014/063594, filed on May 22, 2014.

(30) Foreign Application Priority Data

Sep. 4, 2013 (JP) .................................. 2013-183288

(51) Int. Cl.
*B06B 1/06* (2006.01)
*H01R 43/28* (2006.01)
(Continued)

(52) U.S. Cl.
CPC .............. *B06B 1/0685* (2013.01); *A61B 8/12* (2013.01); *B06B 1/0607* (2013.01);
(Continued)

(58) Field of Classification Search
CPC ... B06B 1/0607; B06B 1/0622; B06B 1/0685; B06B 1/0633; G01K 11/002;
(Continued)

(56) References Cited

U.S. PATENT DOCUMENTS

| 4,778,950 A * | 10/1988 | Lee ...................... H01R 43/007 174/260 |
| 5,267,221 A | 11/1993 | Miller et al. |
| 6,467,138 B1 * | 10/2002 | Aime ................... G10K 11/002 29/25.35 |
| 2006/0231939 A1 * | 10/2006 | Kawabata ........... H01L 23/5385 257/686 |

FOREIGN PATENT DOCUMENTS

| EP | 0559963 A2 | 9/1993 |
| JP | S63-318010 A | 12/1988 |

(Continued)

OTHER PUBLICATIONS

International Search Report dated Jul. 8, 2014 issued in PCT/JP2014/063594.

(Continued)

*Primary Examiner* — A. Dexter Tugbang (74) *Attorney, Agent, or Firm* — Scully, Scott, Murphy & Presser, PC (57) ABSTRACT

A method for manufacturing an ultrasound transducer includes a first step of manufacturing a wiring layer by arranging insulating fibers on conductive threads, a second step of electrically connecting one end of the plurality of conductive threads to a transducer array unit, a third step of providing a first backing material after providing a second backing material so that at least connection sites between the transducer array unit and the conductive threads are embedded, and a fourth step of curing the first backing material so as to fix the transducer array unit and the wiring layer.

5 Claims, 12 Drawing Sheets (51) Int. Cl.
*H01L 23/538* (2006.01)
*H01R 43/00* (2006.01)
*A61B 8/12* (2006.01)

(52) U.S. Cl.
CPC .......... *B06B 1/0622* (2013.01); *B06B 1/0633* (2013.01); *H01L 23/5385* (2013.01); *H01L 23/5389* (2013.01); *H01R 43/007* (2013.01); *H01R 43/28* (2013.01); *Y10T 29/42* (2015.01); *Y10T 29/49005* (2015.01); *Y10T 29/49147* (2015.01); *Y10T 29/49194* (2015.01)

(58) Field of Classification Search
CPC .............. G01K 11/004; H01L 23/5385; H01L 23/5389; H01R 43/007; H01R 43/28; Y10T 29/42; Y10T 29/49005; Y10T 29/49147; Y10T 29/49194; A61B 8/12
See application file for complete search history.

(56) References Cited

FOREIGN PATENT DOCUMENTS

| JP | H02-271843 | A |   | 11/1990 |
|----|------------|---|---|---------|
| JP | H06-046497 | A |   | 2/1994  |
| JP | 2004040250 | A | * | 2/2004  |
| JP | 2007-307289| A |   | 11/2007 |

OTHER PUBLICATIONS

Japanese Office Action dated Aug. 18, 2015 issued in JP 2014-549268.

* cited by examiner

METHOD FOR MANUFACTURING ULTRASOUND TRANSDUCER

CROSS REFERENCE TO RELATED APPLICATION

This application is a continuation application of PCT/JP2014/063594 filed on May 22, 2014 and claims benefit of Japanese Application No. 2013-183288 filed in Japan on Sep. 4, 2013, the entire contents of which are incorporated herein by this reference.

BACKGROUND OF THE INVENTION

1. Field of the Invention

The present invention relates to a method for manufacturing an ultrasound transducer, and more specifically, to a method for manufacturing an ultrasound transducer wired to an electrode.

2. Description of the Related Art

Conventionally, ultrasound diagnostic apparatuses are available which transmit ultrasound to a subject such as a human body using an ultrasound endoscope or the like, receive an echo reflected by the subject and apply signal processing thereto to thereby acquire tomographic images of an interior of the subject. Such ultrasound diagnostic apparatuses are widely used in medical diagnostic fields because of an advantage that image information on tomographic images of the interior of the subject can be obtained non-invasively and instantaneously.

An ultrasound transducer used for such an ultrasound endoscope is configured by arranging a plurality of transducer elements in an array, but as denoted by reference numeral 60 in Japanese Patent Application Laid-Open Publication No. 2007-307289, wiring for ultrasound transmission/reception needs to be connected to individual transducer elements.

SUMMARY OF THE INVENTION

A method for manufacturing an ultrasound transducer according to an aspect of the present invention includes a first step of manufacturing a wiring layer with insulating fibers arranged on a plurality of conductive threads to hold the conductive threads spaced apart from each other by a predetermined distance, a second step of electrically connecting one end of the plurality of conductive threads to a transducer array unit having a plurality of electrodes provided on an acoustic radiation face that radiates ultrasound and on a rear side of the acoustic radiation face, a third step of providing a fluid and curable first backing material that attenuates unnecessary ultrasound after providing a rigid second backing material that attenuates unnecessary ultrasound so that at least connection sites between the transducer array unit and the conductive threads are embedded, and a fourth step of curing the first backing material so as to fix the transducer array unit and the wiring layer.

DETAILED DESCRIPTION OF THE PREFERRED EMBODIMENT

Hereinafter, an embodiment of the present invention will be described with reference to the accompanying drawings.

Figure 1:
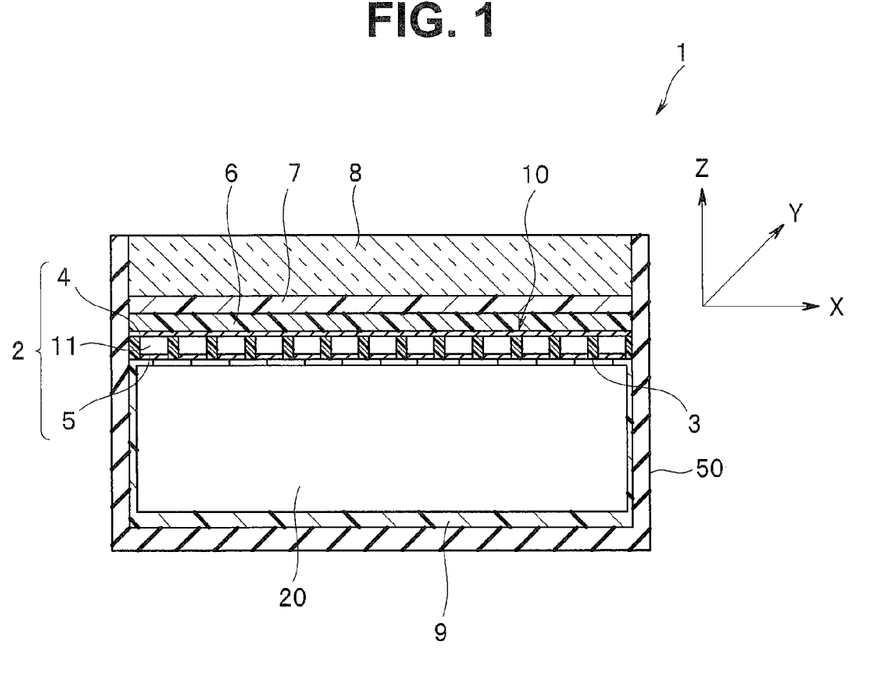
FIG. 1 is a diagram illustrating a schematic configuration of an ultrasound transducer.

In FIG. 1, reference numeral 1 denotes an ultrasound transducer configured by providing, in a housing 50, a transducer array unit 10 including a plurality of transducer elements 2 that radiate ultrasound in a Z direction and receive sound waves reflected from a subject region arranged in an X direction. The transducer element is a minimum unit that transmits/receives ultrasound. Examples of the transducer element 2 include a piezoelectric type one having a publicly known piezoelectric element sandwiched between an upper electrode and a lower electrode or a capacitance type one having an upper electrode and a lower electrode spaced apart from each other by a predetermined distance across a column. The material of the housing 50 is not particularly limited, but electrical safety can be improved by forming the housing 50 using an insulating member, for example.

Note that an example will be described in the present embodiment where a plurality of transducer elements 2 extending in a Y direction and formed into an elongated prismatic shape, called a 2-2 structure in a composite piezoelectric unit field are fixed by an insulating member 3 of resin or the like at a predetermined interval in the X direction to form a transducer array unit 10. However, the structure is not limited to this, but, for example, columnar or strip-shaped transducer elements may be fixed by resin at a predetermined interval to form the transducer array unit 10 having a 2-3 structure or other structures may be adopted.

In the transducer array unit 10, an upper electrode 4 is provided on a top surface side making up an acoustic radiation face of each piezoelectric element 11 and a lower electrode 5 is provided on a bottom surface side which is an opposite side of the acoustic radiation face. In the present embodiment using the piezoelectric type transducer array, the upper electrode 4 of each piezoelectric element 11 is provided as one common electrode and the lower electrode 5 is provided for each piezoelectric element 11 individually.

The upper electrode 4 makes up a GND electrode and the lower electrode 5 makes up a signal transmission/reception signal electrode for each piezoelectric element 11. However, a configuration may also be adopted in which the upper electrode 4 makes up a signal electrode and the lower electrode 5 makes up a GND electrode.

However, in the case of a capacitance type transducer array, if this is described using FIG. 1, the portion corresponding to reference numeral 2 disposed between the upper electrode 4 and the lower electrode 5 is an air gap and the portion corresponding to reference numeral 3 is a columnar member made of an insulating member.

Note that the upper electrode 4 may be formed for each piezoelectric element 11 individually or may be provided so as to be shared by a predetermined number of piezoelectric elements 11.

Furthermore, in the housing 50, a first acoustic matching layer 6 is provided in the Z direction connecting a top surface and a bottom surface of the transducer element 2, above the upper electrode 4, or more specifically, on a top surface of the upper electrode 4 and a second acoustic matching layer 7 is provided on a top surface of the first acoustic matching layer 6. Furthermore, an acoustic lens 8 is provided on a top surface of the second acoustic matching layer 7.

Note that in the ultrasound transducer 1, although the first acoustic matching layer 6, the second acoustic matching layer 7 and the acoustic lens 8 are not always necessary, FIG. 1 shows an example where the first acoustic matching layer 6, the second acoustic matching layer 7 and the acoustic lens 8 are provided.

Figure 2:
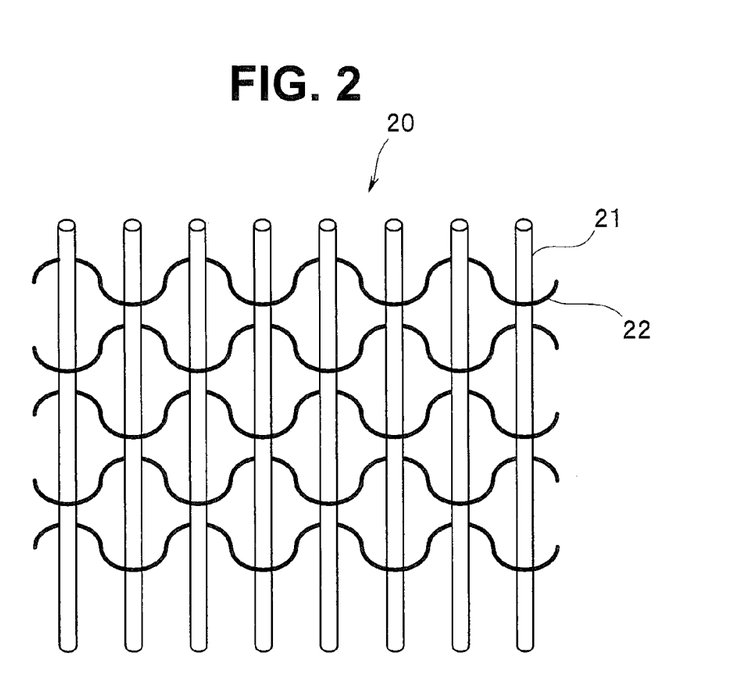
FIG. 2 is a diagram illustrating a basic configuration of a wiring layer.

Furthermore, in the housing 50, a cloth-like wiring layer 20 is disposed below each transducer element 2 on a bottom surface side. As shown in FIG. 2, the wiring layer 20 is formed as a flexible cloth-like member formed using a plurality of conductive threads 21 which are conductive members making up signal lines and a plurality of insulating fibers 22 which are insulating members that hold the respective conductive threads 21 while keeping a predetermined distance between the respective conductive threads 21 so as not to contact each other.

In the present embodiment, the wiring layer 20 is formed into a cloth-like shape by combining the insulating fibers 22 and the thread-like conductive threads 21 in a matrix, and is flexible. The insulating fiber 22 is formed so as to be interposed between the neighboring conductive threads 21 to prevent the neighboring conductive threads 21 from contacting each other, and "cloth-like" may mean "woven fabric" or "non-woven fabric."

Note that the conductive thread 21 is not limited to the thread-like form but may be a swath-like form, and the conductive thread 21 may be not linear but undulated if contact with the neighboring conductive threads 21 is prevented.

The insulating fiber 22 may be a thread-like form, swath-like form or felt-like form. The insulating fiber 22 may be a material having high thermal conductivity capable of efficiently dissipating heat of the transducer element 2 and the conductive thread 21. Examples of the material of the insulating fiber include Keplerian fiber and aramid fiber. These materials have an advantage of having excellent strength.

Each conductive thread 21 of the wiring layer 20 has one end connected to the lower electrode 5 of each transducer element 2 and the other end connected to a signal cable extending from, for example, an ultrasound observing apparatus. A pulse signal transmitted from the ultrasound observing apparatus is transmitted to the lower electrode 5 via the conductive thread 21 and a received signal from the transducer element 2 is transmitted to the signal cable via the conductive thread 21.

Figure 3A:
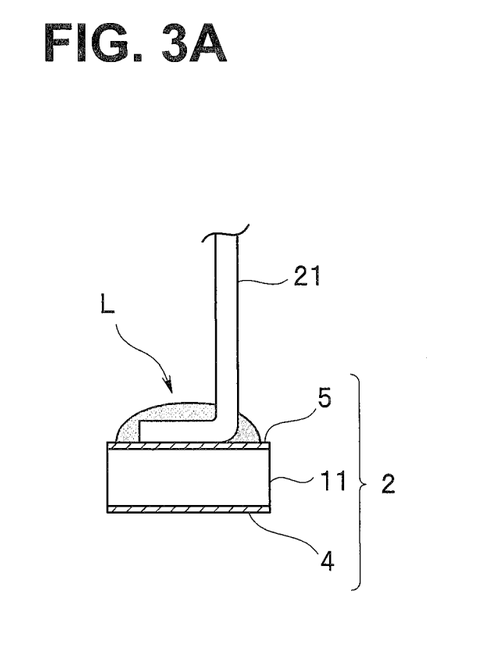
FIG. 3A is a diagram illustrating wiring to a transducer element.
Figure 3B:
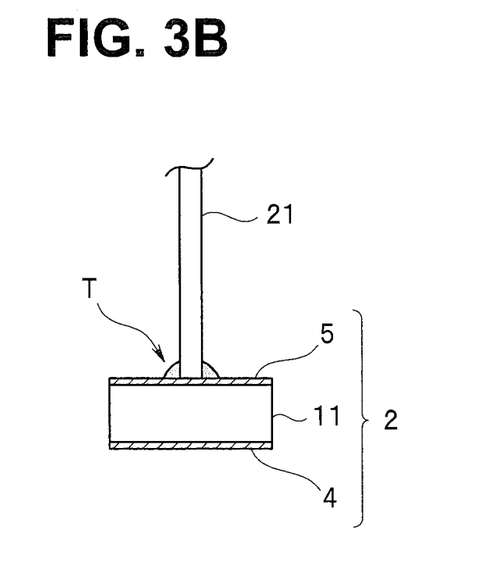
FIG. 3B is a diagram illustrating wiring to a transducer element.

The transducer element 2 and the conductive thread 21 are connected together using, for example, a method illustrated in FIGS. 3A and 3B. In the example shown in FIG. 3A, a distal end portion of the conductive thread 21 is slightly bent, caused to creep along the lower electrode 5 of the transducer element 2, and in a portion L where both parts overlap, both the parts are mechanically fixed using solder, conductive adhesive or plating and electrically connected together. On the other hand, in the example shown in FIG. 3B, an end face of the distal end portion of the conductive thread 21 is struck against the lower electrode 5 of the transducer element 2, and in a striking portion T, the end face and the lower electrode 5 are fixed using solder, conductive adhesive or plating and electrically connected together.

Figure 4:
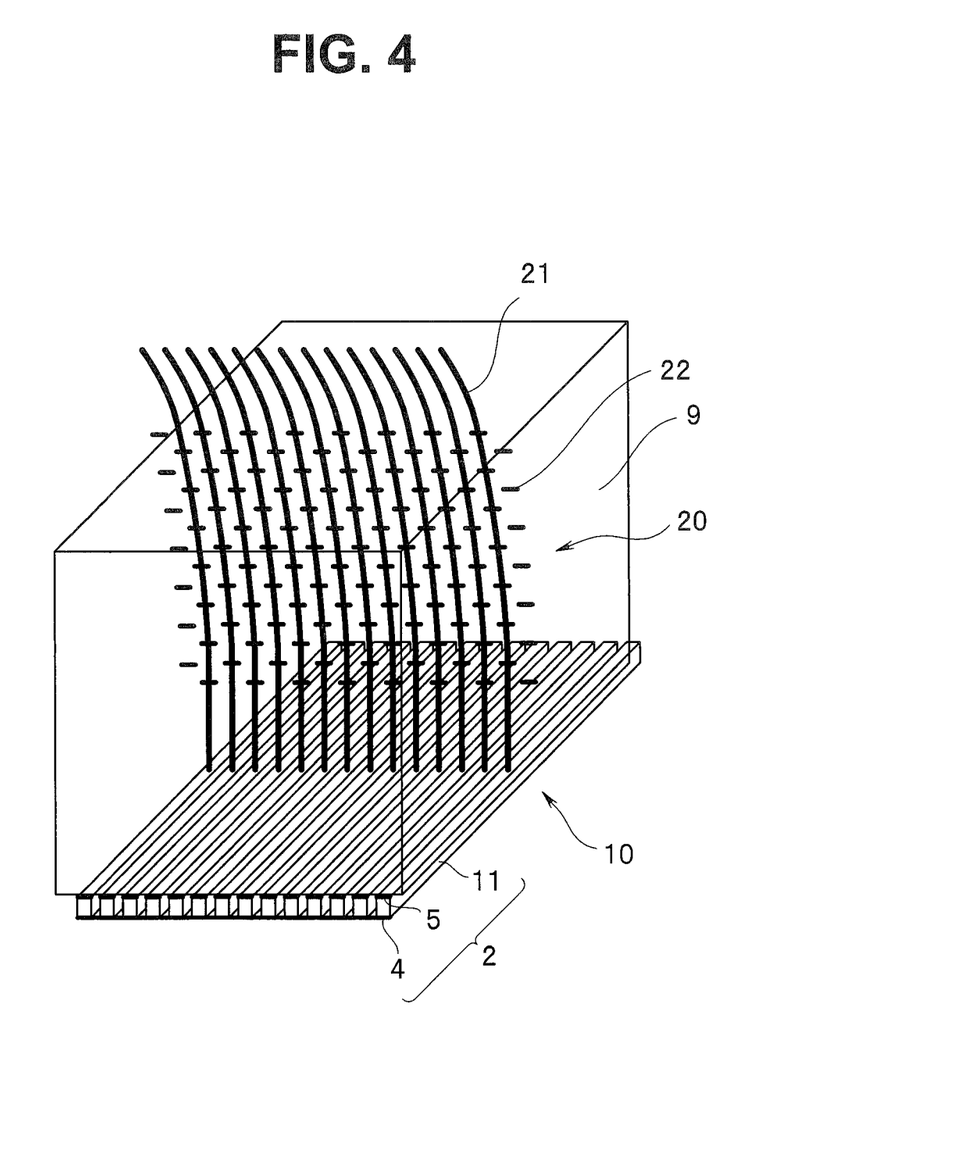
FIG. 4 is a diagram illustrating a backing material in which a wiring layer is embedded.

In the housing 50, a backing material 9 that attenuates unnecessary ultrasound is provided below the lower electrode 5 of the transducer element 2 in the Z direction. As shown in FIG. 4, the backing material 9 is provided so that a portion of the wiring layer 20 electrically connected to at least the lower electrode 5 is embedded and functions as a fixing portion that fixes the transducer array unit 10 and the wiring layer 20 to the housing 50 in addition to the unnecessary ultrasound attenuating function. As for the backing material 9 and the insulating fiber 22, in order to prevent reflection by the insulating fiber 22, a reflection factor calculated from (Equation 1) where an acoustic impedance of the backing material 9 is assumed to be $Z_1$ and an acoustic impedance of the insulating fiber 22 is assumed to be $Z_2$, is preferably small, is preferably, for example, equal to or smaller than 0.3 and more preferably 0.

$$\text{Reflection factor} = |(Z_2 - Z_1)/(Z_2 + Z_1)| \qquad \text{(Equation 1)}$$

A gap between the conductive thread 21 and the insulating fiber 22 forming the wiring layer 20 has such roughness that the backing material 9 can be inserted therebetween and when a relatively hard material is used as the material forming the backing material 9, it is preferable to use a material which is initially in liquid form having fluidity but is cured after filling (e.g., epoxy resin) as an adhesive that is inserted into the gap between the conductive thread 21 and the insulating fiber 22 to bond both the parts. The acoustic impedance of the adhesive is preferably substantially on the same level with that of the backing material 9.

Moreover, in addition to the backing material 9 as the adhesive, a casting type material is used as the backing material 9 and a material which is in liquid form having fluidity at the time of filling and cured after filling is used so as to be charged into the gap between the conductive thread 21 and the insulating fiber 22. More specifically, the backing material 9 may be formed using gel epoxy or silicone, urethane or various flexible resin materials such as various types of elastomer or using the aforementioned resin material as a base, composed with a filler member such as alumina, zirconia or titanium oxide through casting. Furthermore, a catalyst for curing may also be included. As the curing method, conventional publicly known techniques such as thermosetting or photosetting may be used.

Furthermore, curing itself need not be performed or curing may be stopped before curing is completed and a state with certain fluidity still kept may be considered as a final form.

Here, the wiring layer 20 formed of the conductive threads 21 and the insulating fibers 22 is formed into a cloth-like shape in the present embodiment as described above, but the weaving method does not particularly matter if it is a method capable of keeping a distance that can secure insulation between the respective conductive threads 21. The insulating fiber 22 preferably has an undulating shape or the like so as to cause sound waves from the transducer element 2 to scatter in directions other than the element direction. Moreover, the wiring layer 20 may also be formed as a so-called non-woven fabric formed by bonding or intertwining the conductive threads 21 to/with the insulating fibers 22 by means of thermal, mechanical or chemical action.

Figure 5:
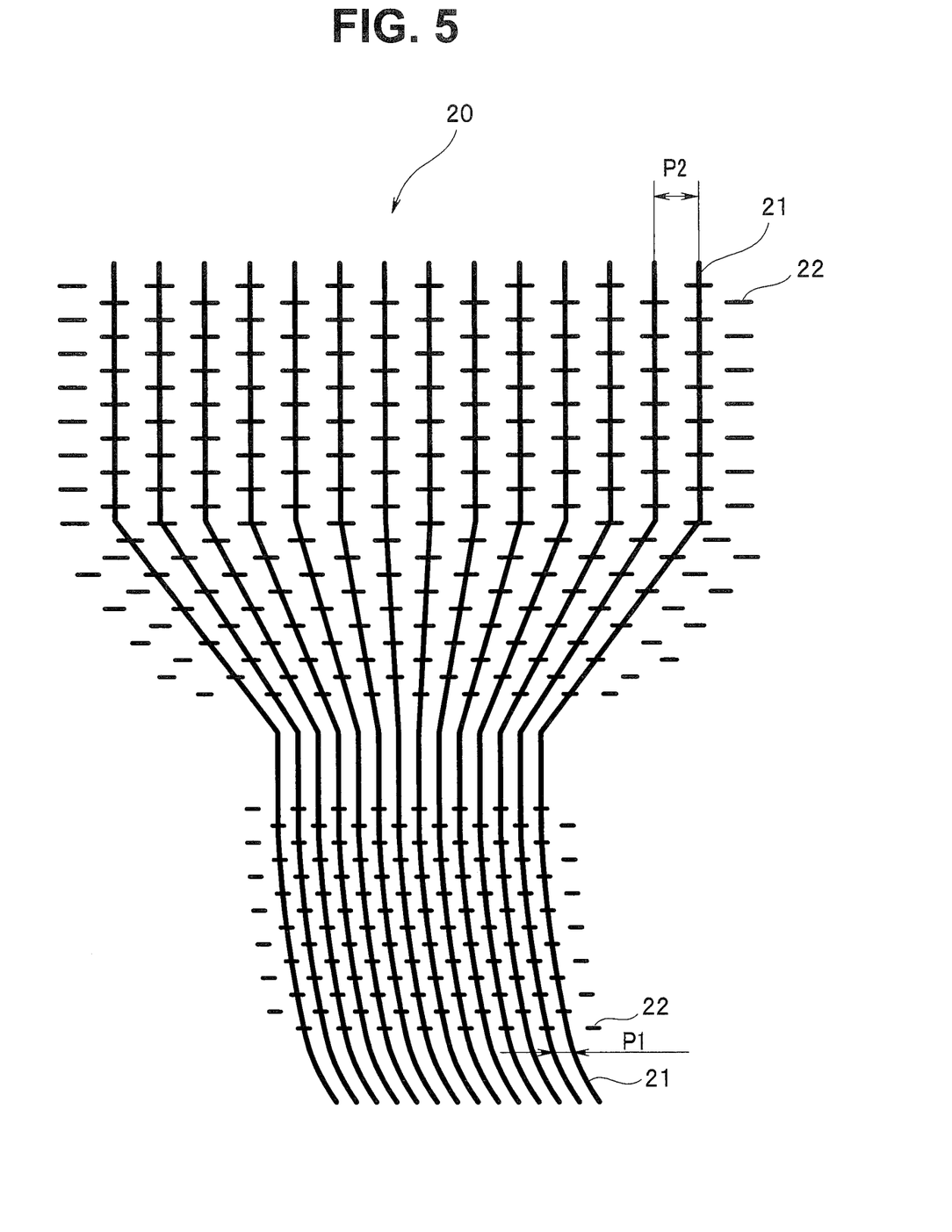
FIG. 5 is a diagram illustrating an array pitch of a plurality of conductive threads.

Furthermore, the array of the plurality of conductive threads 21 is basically a uniform pitch, but if the plurality of conductive threads 21 are spaced apart at a predetermined pitch as shown in FIG. 5, the pitch need not be fixed. In an example in FIG. 5, a pitch p1 of the conductive threads 21 in the vicinity of the transducer element determined according to the interval of the transducer elements is increased to a pitch p2 (p2>p1) in a region distant from the transducer element.

In this case, by adjusting the thickness (width, thickness) of the material making up the insulating fiber 22 within a range of several μm to several tens of μm, the pitch of the conductive threads 21 can be adjusted. The insulating fiber 22 may be configured by mixing other finer insulating materials or the like with the insulating material having a thickness for adjusting the pitch of the conductive threads 21. By so doing, it is possible to increase an anchor effect by the backing material 9 or adhesive being embedded in the gap between the insulating fibers 22 in a complicated manner, prevent deterioration of acoustic characteristics resulting from exfoliation between the backing material 9 and the conductive thread 21 and also omit the backing material 9.

Figure 6:
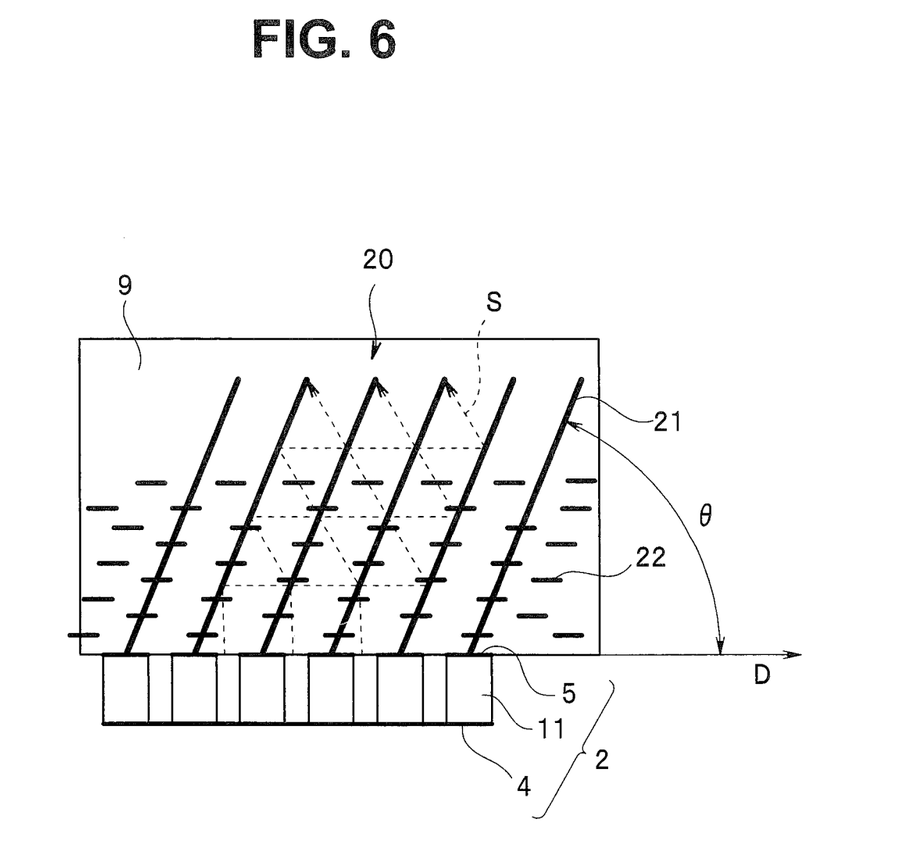
FIG. 6 is a diagram illustrating a wiring angle of the conductive threads.

Furthermore, as shown in FIG. 6, the conductive threads 21 of the wiring layer 20 need not be wired perpendicular to an array direction (D) in which a plurality of lower electrodes of the transducer elements 2 are arrayed, but may be wired at a predetermined angle θ, in a direction neither parallel nor perpendicular to the array direction (D). Particularly, since the conductive threads 21 are wired in the direction neither parallel nor perpendicular to the array direction (D) from the connection portion with the lower electrode to a predetermined distance, ultrasound radiated onto the rear side of the transducer element 2 passes through a path S in which the ultrasound is propagated while being reflected in zigzag between wires in the wiring layer 20, and even when the thickness of the backing material 9 is small, it is possible to extend the propagation distance of unnecessary sound waves and effectively attenuate the unnecessary sound waves.

Figure 7:
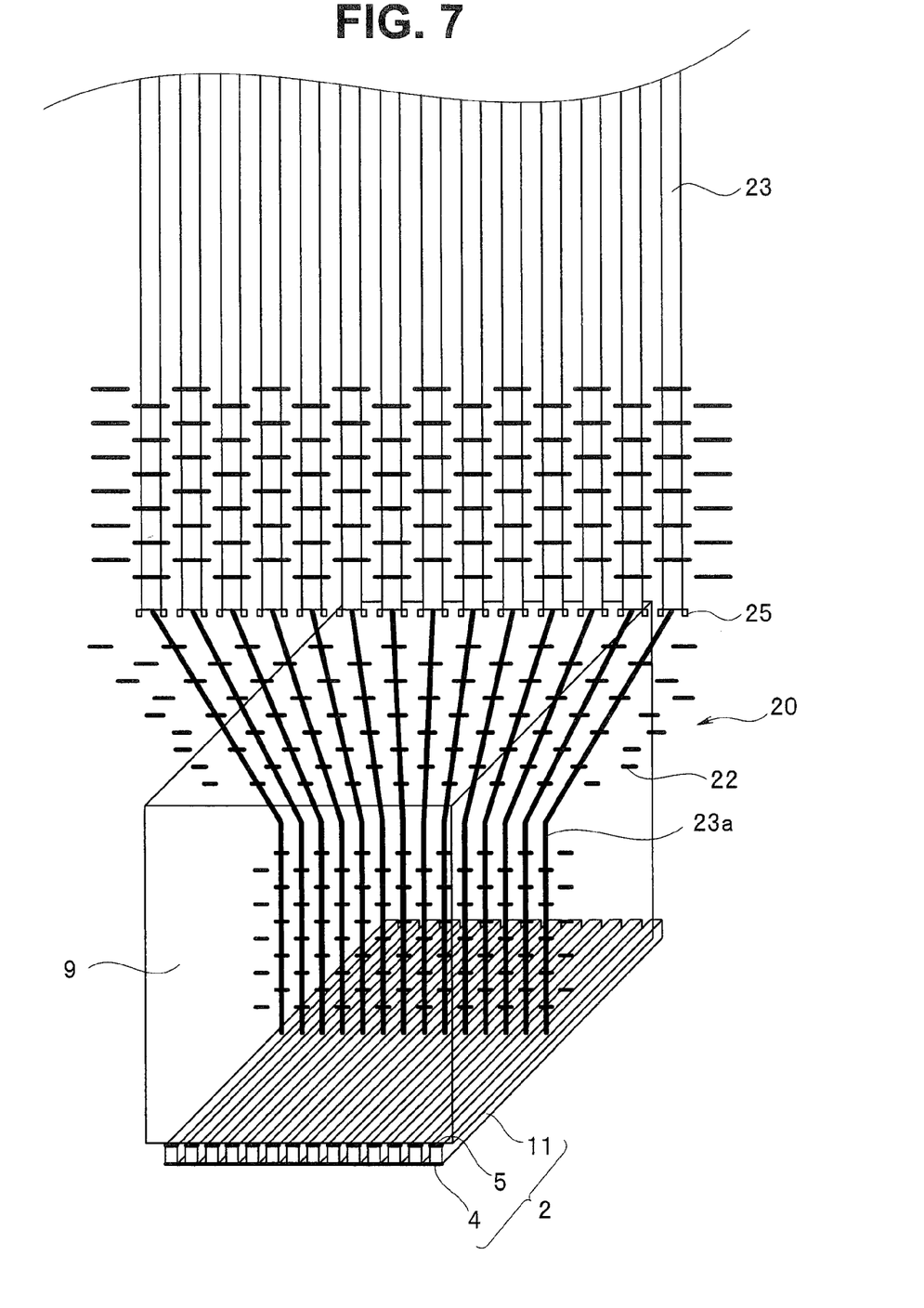
FIG. 7 is a diagram illustrating a wiring layer constructed of a plurality of coaxial lines.

Furthermore, as shown in FIG. 7, it may be possible to expose core wires 23a of the plurality of coaxial lines 23 which are signal cables and use them as the conductive threads 21, and weave the core wires 23a from the insulating fibers 22 to thereby form the wiring layer 20. This makes it possible to directly connect the signal cables to the transducer element 2 and use them while preventing short circuit. Note that when ground wires of the respective coaxial lines 23 are short circuited, connected to the upper electrodes 4 of the respective transducer elements 2 and used, it may be possible to weave conductive members 25 into the grounding wires of the respective coaxial lines 23 to form a short-circuited ground wiring portion.

Figure 8:
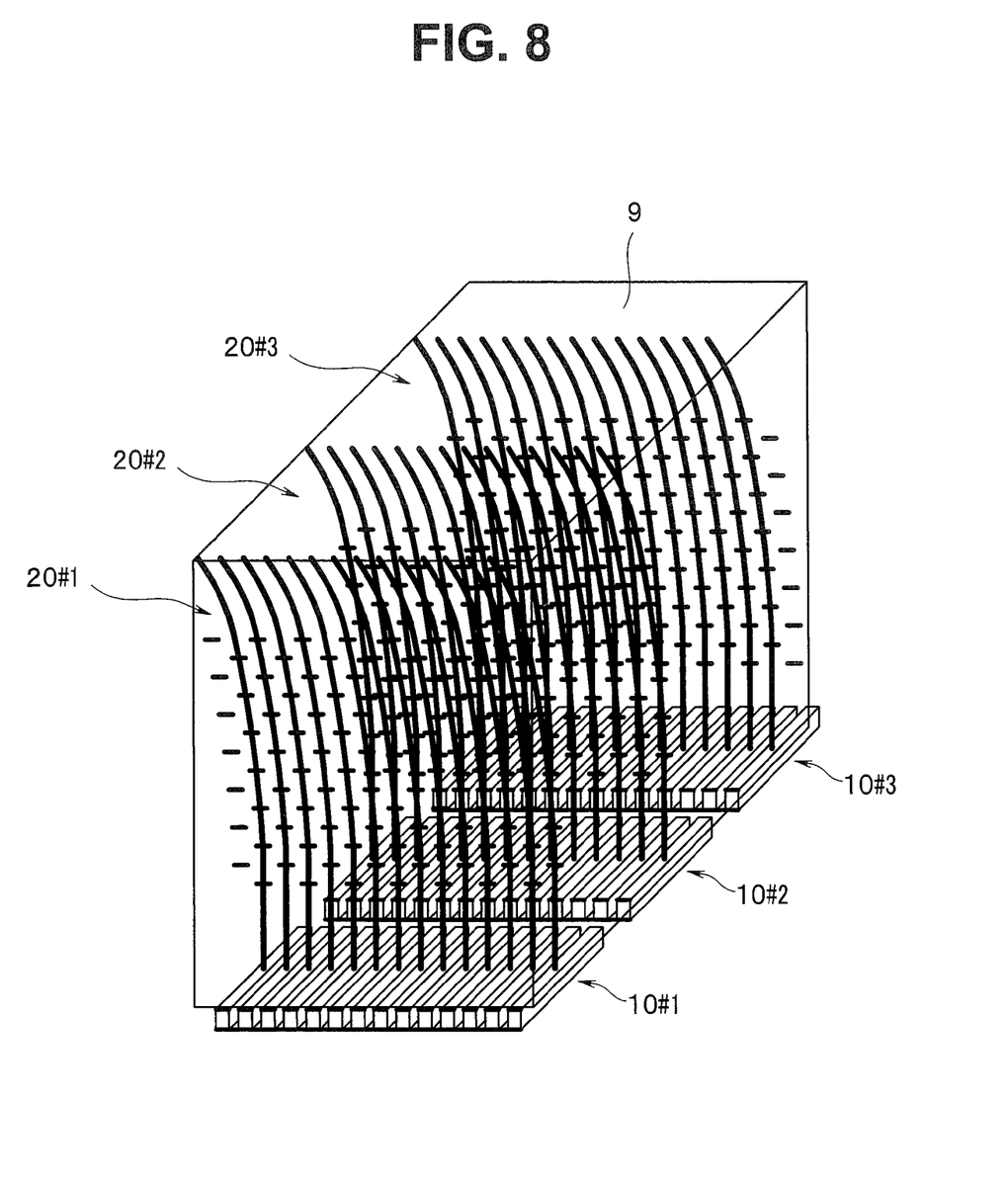
FIG. 8 is a diagram illustrating a plurality of wiring layers applied to a matrix array.

Furthermore, as shown in FIG. 8, when the transducer elements 2 are arranged as a matrix array, this can be done using the wiring layer 20 in plurality. In FIG. 8, three wiring layers 20#1, 20#2 and 20#3 are embedded and laminated in the backing material 9 in correspondence with transducer array units 10#1, 10#2 and 10#3 that form a matrix. The respective wiring layers 20 are prevented from contacting each other because the insulating fibers 22 are disposed so as to prevent the conductive threads 21 from being exposed from the lateral parts.

Figure 14:
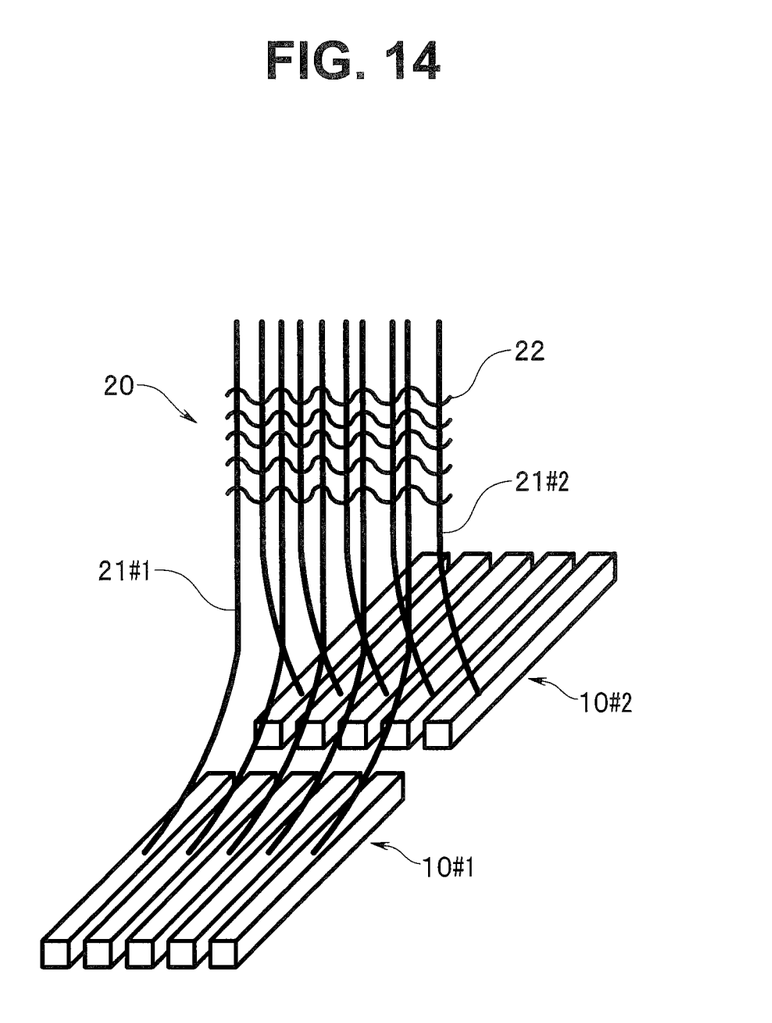
FIG. 14 is a diagram illustrating an example where one wiring layer is shared by a plurality of transducer array units in FIG. 8.

However, the transducer array units 10 and the wiring layers 20 need not always be provided in a one-to-one correspondence but the plurality of transducer array units 10#1 and 10#2 may be configured to share one wiring layer 20 as shown in FIG. 14.

In FIG. 14, the conductive thread 21#1 electrically connected to the transducer array unit 10#1 and the conductive thread 21#2 electrically connected to the transducer array unit 10#2 are woven from the same insulating fibers 22 so as not to contact each other.

Next, an example where the above-described ultrasound transducer 1 is provided in an endoscope will be described using FIG. 9 to FIG. 13. Note that the ultrasound transducer 1 will be described hereinafter as an ultrasound transducer unit assembled into the endoscope.

Figure 9:
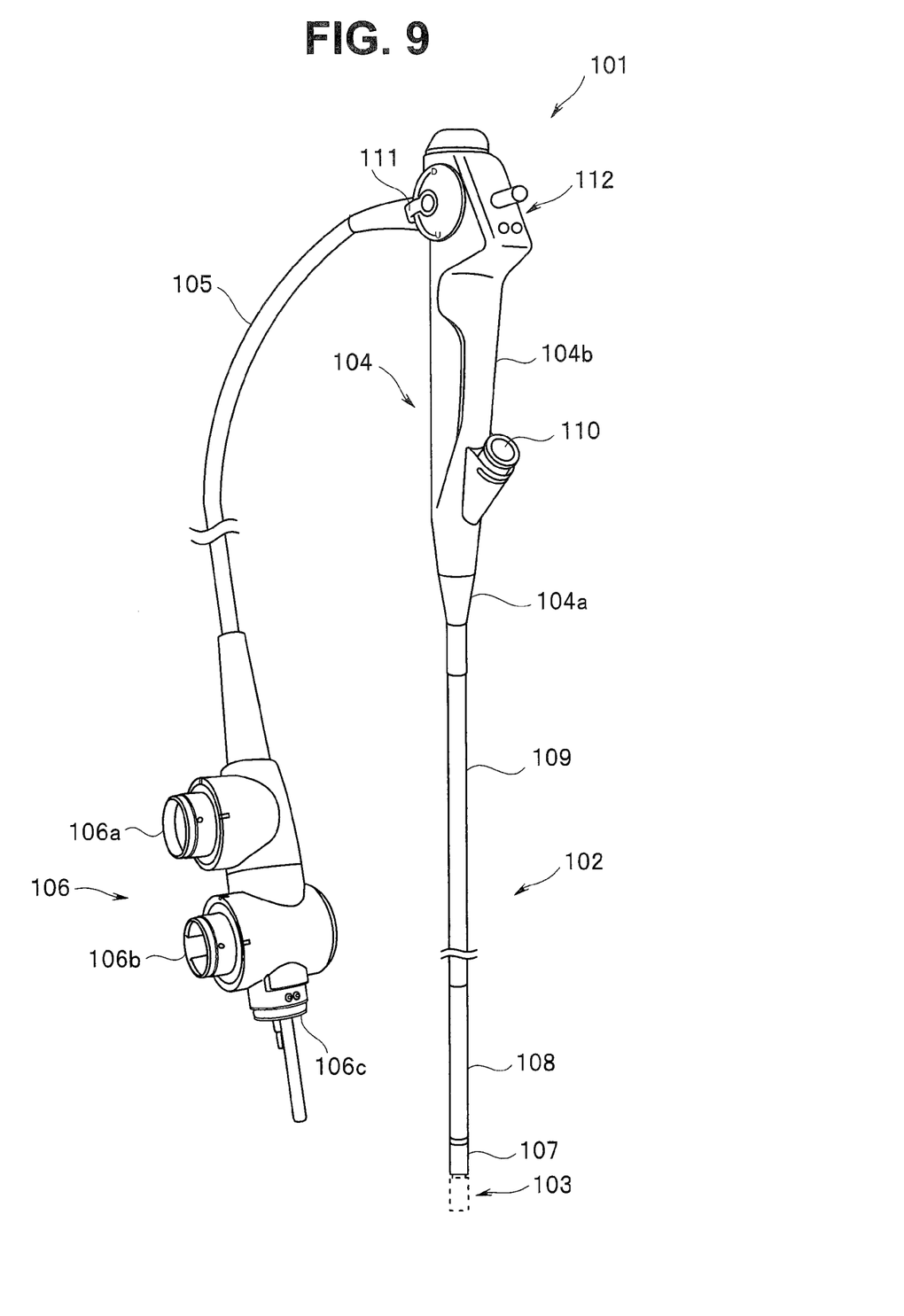
FIG. 9 is a schematic diagram of an ultrasound endoscope.

An ultrasound endoscope 101 shown in FIG. 9 is provided with an ultrasound transducer unit 103 on a distal end side of an elongated tube insertion portion 102 inserted into a subject. An operation portion 104 that also serves as a grasping portion is connected on a proximal end side of the insertion portion 102 of the ultrasound endoscope 101 and a connector portion 106 is disposed on a distal end side of a universal cord 105 extending from a lateral part of the operation portion 104.

The insertion portion 102 is configured by including a rigid portion 107 connected to an ultrasound transducer unit 103 on a distal end side, a bending portion 108 connected on a rear end side of the rigid portion 107 and configured to freely bend, for example, in an up-down direction and a flexible tube portion 109 connected on a rear end side of the bending portion 108. The flexible tube portion 109 is provided in a section from the bending portion 108 to the operation portion 104 and is a thin and long tube member formed with flexibility so as to be passively flexible.

The operation portion 104 includes a bend preventing portion 104a connected to the flexible tube portion 109 so as to cover a proximal end of the flexible tube portion 109 and a grasping portion 104b connected to the bend preventing portion 104a for the user to grasp by the hand when using the ultrasound endoscope 101. Various operation members are disposed on a top end side of the grasping portion 104b and a treatment instrument insertion port 110 or the like to guide a treatment instrument into the subject is provided at a location on a bottom end side of the grasping portion 104b and above the bend preventing portion 104a. Examples of the operation members provided in the operation portion 104 include a bending lever 111 that performs bending operation of the bending portion 108 and a plurality of operation buttons 112 to perform various operations corresponding to air/water feeding operation, suction operation, image pickup or illumination or the like.

The universal cord 105 is a composite cable that runs from a distal end of the insertion portion 102 through the bending portion 108 and the flexible tube portion 109 to the operation portion 104, and further passes various signal lines extending out of the operation portion 104 through an inside thereof, passes a light guide of a light source apparatus (not shown), and further passes an air/water feeding tube that extends out of an air/water feeding apparatus (not shown). A connector portion 106 disposed on a distal end side of the universal cord 105 is configured by including an ultrasound connector 106a that makes a connection with an ultrasound observing apparatus (not shown), an electric connector portion 106b to which various signal cables are connected and a light source side connector 106c that makes a connection with the light source apparatus and the air/water feeding apparatus (not shown).

Figure 10:
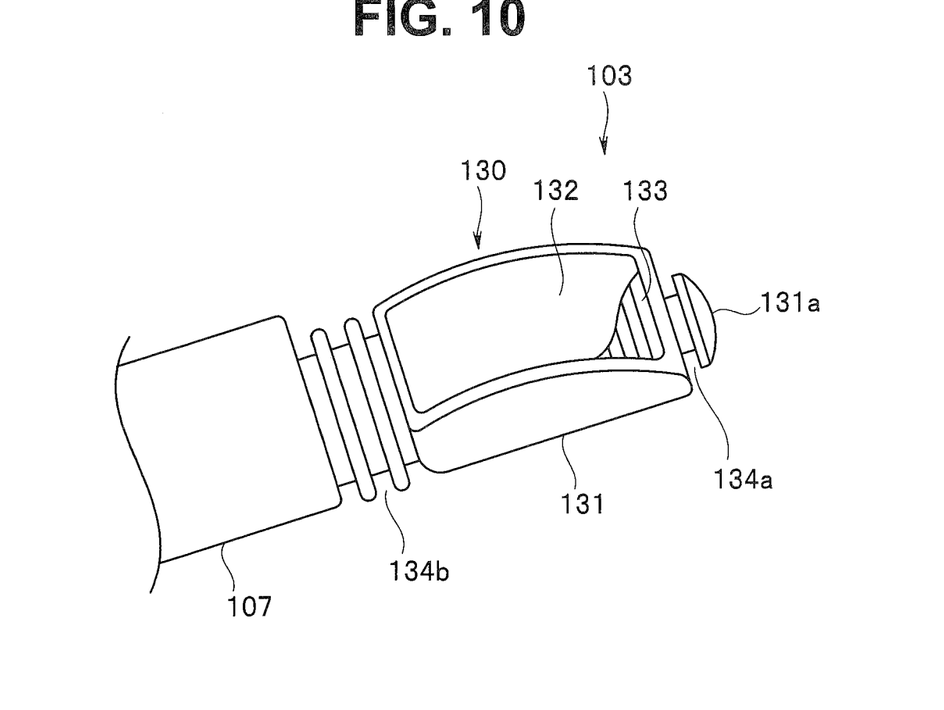
FIG. 10 is a diagram illustrating a convex type ultrasound transducer unit.

On the other hand, when the ultrasound transducer unit 103 connected to the rigid portion 107 on a distal end side of the insertion portion 102 is, for example, a convex type transducer unit, it is configured by including a transducer array unit 130 and a nosepiece 131 which is a housing that accommodates the transducer array unit 130 as shown in FIG. 10. In the transducer array unit 130, an acoustic lens portion 132 that is disposed and held integrally with a notch portion formed in substantially the center of the nosepiece 131 to form a convex type ultrasound scanning surface in a longitudinal axis direction of the insertion portion 102 and a plurality of transducer elements 133 disposed along the convex surface inside the acoustic lens portion 132 form an ultrasound transmission/reception unit.

Note that a substantially cylindrical protruding portion 131a is provided at a distal end of the nosepiece 131, a first balloon holding groove 134a is formed around a perimeter of the protruding portion 131a on a base side and a second balloon holding groove 134b is formed around a perimeter of a coupling portion of the nosepiece 131 with the rigid portion 107.

Between the first balloon holding groove 134a and the second balloon holding groove 134b, a thin and flexible balloon made of, for example, silicon rubber or latex rubber is detachably interposed so as to cover the nosepiece 131.

Although not shown, an objective lens window making up an observation optical system, an illumination lens window making up an illumination optical system and a treatment instrument outlet from which a treatment instrument such as a puncture needle is led out are provided on a distal end side of the rigid portion 107 connected to the second balloon holding groove 134b.

Figure 11:
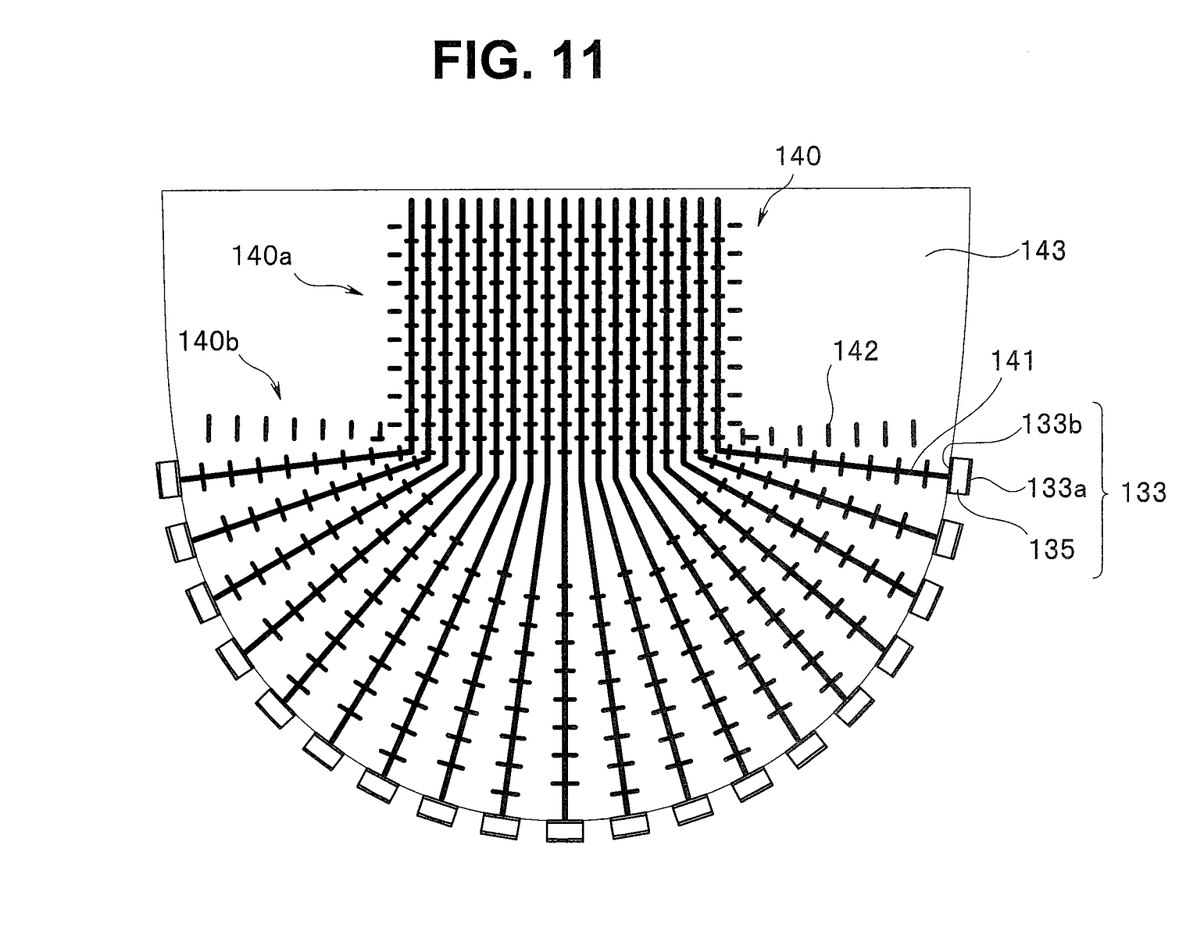
FIG. 11 is a diagram illustrating a wiring example of the convex type ultrasound transducer unit.

The plurality of transducer elements 133 arrayed in a convex shape are connected to a wiring layer 140 as shown in FIG. 11. The wiring layer 140 includes a parallel portion 140a in which a plurality of conductive threads 141 are arrayed in parallel and a development portion 140b in which a distal end side of the parallel portion 140a is developed into a fan-shape in correspondence with the array of the plurality of transducer elements 133.

An interval between the respective conductive threads 141 that gradually increases in the development portion 140b is kept by a plurality of insulating fibers 142 which are woven in a circumferential direction, a distal end portion of each conductive thread 141 is connected to a lower electrode 133b of each transducer element 133 and fixed using solder, conductive adhesive or plating or the like. The wiring layer 140 is embedded and held in a backing material 143. Note that the upper electrode 133a of each transducer element 133 is commonly connected to a GND line. A piezoelectric element 135 is interposed between the lower electrode 133b and the upper electrode 133a.

Figure 12:
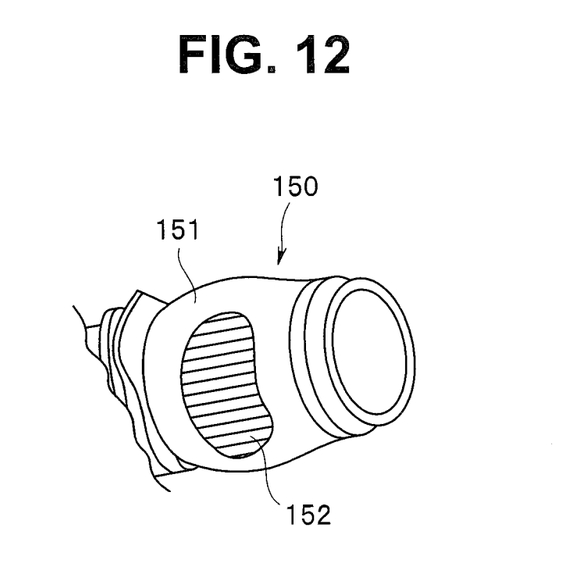
FIG. 12 is a diagram illustrating a radial type ultrasound transducer unit.

When the ultrasound transducer unit 103 is a radial type transducer unit, as shown in FIG. 12, a housing 150 which is, for example, cylindrical and made of polyethylene and whose distal end is closed is connected to the rigid portion 107. An outer wall portion of the cylindrical housing 150 makes up an acoustic lens 151 and a plurality of transducer elements 152 are radially arrayed and held inside the acoustic lens 151.

Hereinafter, a method will be described which extends coaxial lines in a diameter direction and directly wires them to the piezoelectric elements, but a method may also be adopted which wires conductive threads radially arrayed in a diameter direction to coaxial lines via a wiring material fixed by concentric insulating fibers.

A method may be adopted which directly wires core wires of coaxial lines as conductive threads when manufacturing a convex type ultrasound observation unit as well.

Figure 13:
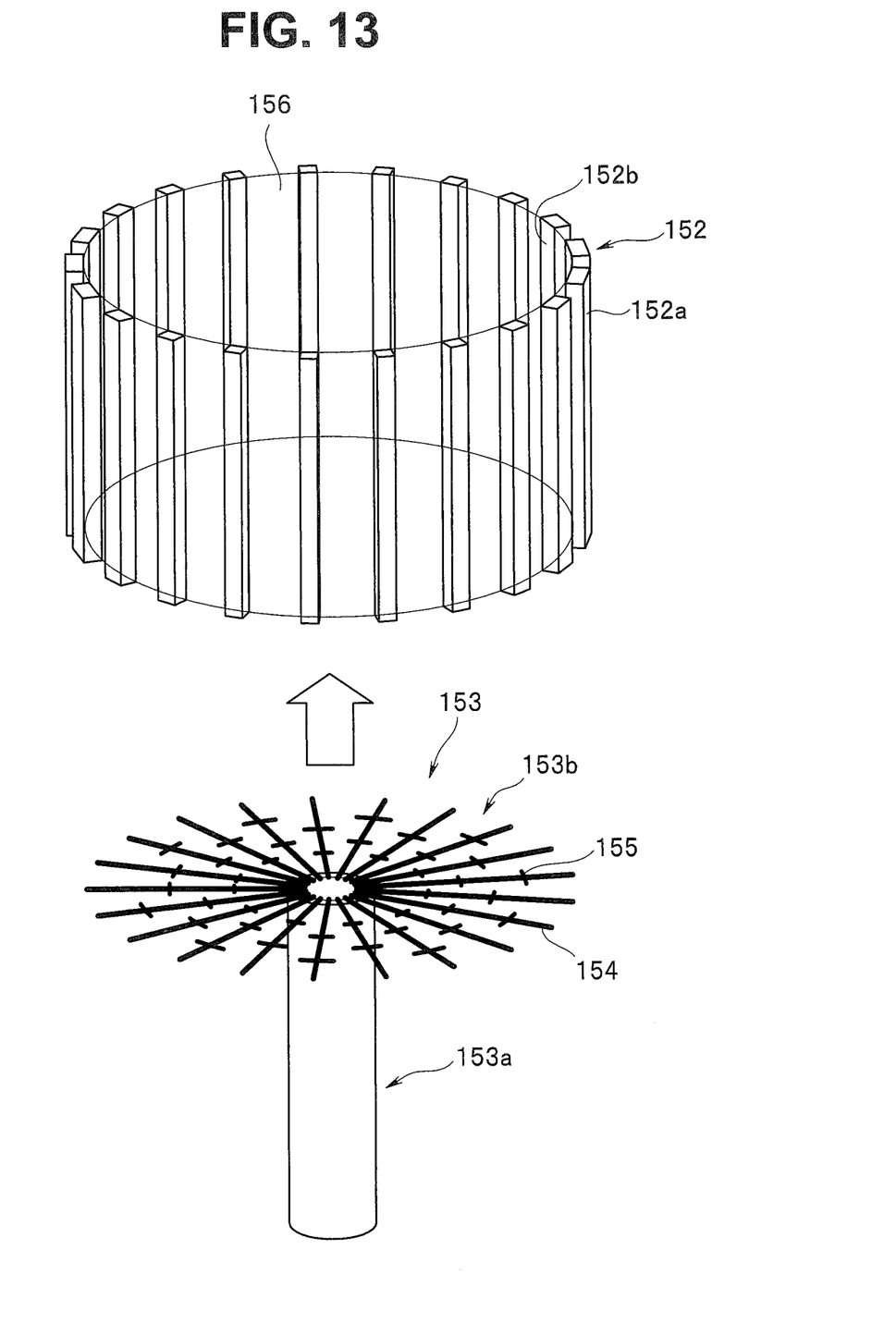
FIG. 13 is a diagram illustrating a wiring example of the radial type ultrasound transducer unit.

The radially arrayed transducer elements 152 are connected to a wiring layer 153 as shown in FIG. 13. The wiring layer 153 can be formed in accordance with the wiring layer 20 using the above-described plurality of coaxial lines in FIG. 7. That is, the wiring layer 153 includes a cable bundle 153a that bundles a plurality of coaxial lines and an expansion portion 153b that causes core wires 154 of respective coaxial lines to be exposed from the cable bundle 153a so as to extend in the diameter direction of the cable bundle 153a and has a plurality of insulating fibers 155 woven between the respective core wires 154 in a circumferential direction.

The expansion portion 153b of the wiring layer 153 is inserted in the plurality of radially arrayed transducer elements 152, a distal end portion of each core wire 154 is connected to a lower electrode 152b of each transducer element 152 and fixed using solder, conductive adhesive, plating or the like. The inside (lower electrode 152b side) of a plurality of radially arrayed transducer elements 152 is filled with a backing material 156 to hold the transducer elements 152 and the wiring layer 153. Note that the upper electrodes 152a of the respective transducer elements 152 are commonly connected to a GND line.

Thus, in the present embodiment, the transducer array unit 10 is wired using the wiring layer 20 including the plurality of conductive threads 21 and the insulating fibers 22 that keep the conductive threads 21 spaced apart from each other by a predetermined distance to prevent the plurality of conductive threads 21 from contacting each other. It is thus possible not only to easily perform wiring regardless of the number of transducer elements, the arrangement or the size thereof and improve operability but also to achieve high-density wiring while preventing short circuits between wiring materials and deterioration of acoustic characteristics.

Moreover, even if the wiring layer 20 is embedded in the backing material or the like and stress is generated due to cure contraction or the like, it is possible to avoid short circuits between the conductive threads 21 and secure damping performance by pouring the backing material into gaps of the woven wiring layer 20. Moreover, the anchor effect of the woven insulating fibers 22 makes it possible to prevent the backing material from exfoliating from the conductive threads 21, causing deterioration of acoustic characteristics. Furthermore, it is also possible to efficiently dissipate heat generated in the transducer array unit 10.

Note that although a piezoelectric type ultrasound transducer including a piezoelectric element interposed between the upper electrode and the lower electrode has been described by way of example, the present invention is not limited to this, but is also applicable to a capacitance type ultrasound transducer including an air gap interposed between the upper electrode and the lower electrode.

What is claimed is:

1. A method for manufacturing an ultrasound transducer, comprising:
a first step of manufacturing a wiring layer with insulating fibers arranged on a plurality of conductive threads to hold the conductive threads spaced apart from each other by a predetermined distance;
a second step of electrically connecting one end of the plurality of conductive threads to a transducer array unit having a plurality of electrodes provided on an acoustic radiation face that radiates ultrasound and on a rear side of the acoustic radiation face;
a third step of providing the wiring layer with a fluid and curable first backing material that attenuates unnecessary ultrasound and is fillable between the conductive threads and the insulating fibers after providing the wiring layer with a rigid second backing material that attenuates unnecessary ultrasound so that at least connection sites between the transducer array unit and the conductive threads are embedded; and
a fourth step of curing the first backing material so as to fix the transducer array unit and the wiring layer.

2. The method for manufacturing the ultrasound transducer according to claim 1, wherein in the second step, the conductive threads are arranged in a direction neither parallel nor perpendicular to an array direction of the electrodes of the transducer array unit from the connection sites to a predetermined distance.

3. The method for manufacturing the ultrasound transducer according to claim 1, wherein in the first step, the insulating fibers are arranged so that the conductive threads are not exposed to a surface, and the wiring layer is provided in plurality.

4. The method for manufacturing the ultrasound transducer according to claim 1, wherein in the first step, the conductive threads are woven with at least one of the insulating fibers.

5. The method for manufacturing the ultrasound transducer according to claim 1, wherein the first step manufactures the wiring layer comprising first insulating fibers that hold the plurality of conductive threads spaced apart from each other by a predetermined distance and second insulating fibers thinner than the first insulating fibers, the first insulating fibers and the second insulating fibers being arranged on the conductive threads.

* * * * *